United States Patent
Lucas et al.

(10) Patent No.: US 6,834,264 B2
(45) Date of Patent: Dec. 21, 2004

(54) METHOD AND APPARATUS FOR VOICE DICTATION AND DOCUMENT PRODUCTION

(75) Inventors: Mark Lucas, Roanoke, VA (US); Stephen Miko, Roanoke, VA (US); Steven A. Bennington, Roanoke, VA (US)

(73) Assignee: Provox Technologies Corporation, Roanoke, VA (US)

( * ) Notice: Subject to any disclaimer, the term of this patent is extended or adjusted under 35 U.S.C. 154(b) by 533 days.

(21) Appl. No.: 09/901,906

(22) Filed: Jul. 11, 2001

(65) Prior Publication Data

US 2002/0143533 A1 Oct. 3, 2002

Related U.S. Application Data (60) Provisional application No. 60/279,458, filed on Mar. 29, 2001.

(51) Int. Cl.[7] .............................................. G10L 15/26
(52) U.S. Cl. ...................... 704/235; 704/270; 379/88.01
(58) Field of Search ................................ 704/235, 270, 704/275; 379/88.01; 705/3

(56) References Cited

U.S. PATENT DOCUMENTS

| | | | |
|---|---|---|---|
| 5,146,439 A | * | 9/1992 | Jachmann et al. ........ 369/25.01 |
| 5,148,366 A | * | 9/1992 | Buchanan et al. ........... 715/531 |
| 5,267,155 A | * | 11/1993 | Buchanan et al. ........... 715/540 |
| 5,519,808 A | | 5/1996 | Benton, Jr. et al. ........ 395/2.79 |
| 5,526,407 A | | 6/1996 | Russell et al. |
| 5,530,950 A | | 6/1996 | Medan et al. |
| 5,772,585 A | | 6/1998 | Lavin et al. |
| 5,818,800 A | | 10/1998 | Barker ......................... 369/25 |
| 5,857,099 A | | 1/1999 | Mitchell et al. ............. 704/235 |
| 5,909,667 A | | 6/1999 | Leontiades et al. ......... 704/275 |
| 5,960,399 A | | 9/1999 | Barclay et al. |
| 5,960,447 A | | 9/1999 | Holt et al. |
| 5,995,936 A | | 11/1999 | Brais et al. |
| 6,122,614 A | | 9/2000 | Kahn et al. |
| 6,128,002 A | | 10/2000 | Leiper |
| 6,259,657 B1 | * | 7/2001 | Swinney ...................... 704/270 |
| 6,282,154 B1 | * | 8/2001 | Webb .......................... 704/275 |

\* cited by examiner

*Primary Examiner*—Daniel Abebe
(74) *Attorney, Agent, or Firm*—Kenyon & Kenyon (57) ABSTRACT

Multiple documents including multiple fields may be produced using a voice recognition engine to transcribe dictated notes. An embodiment of an apparatus to generate documents from a user's dictation may include a computer interface and a computer in communication with the computer interface including a voice recognition engine, a database, and a memory. A method of entry of dictation into a plurality of documents may include receiving an indication of a selection of a plurality of documents from a list of documents, receiving an indication of a field descriptor of a first field in a document, receiving dictated speech to be entered into the first field, writing transcribed text representative of the dictated speech to the first field, and writing the transcribed text to other fields having the same descriptor in each of the other selected plurality of documents.

27 Claims, 8 Drawing Sheets

METHOD AND APPARATUS FOR VOICE DICTATION AND DOCUMENT PRODUCTION

This application claims benefit of the filing date of U.S. Provisional Application Ser. No. 60/279,458, filed Mar. 29, 2001, entitled "Method and Apparatus for Voice Dictation and Document Production," and incorporated herein by reference in its entirety.

FIELD OF THE INVENTION

The invention relates to the field of document production by dictation, voice-to-text conversion, and automated processing.

BACKGROUND

In general, methods of authoring a document have changed little in the past forty years. A typical example may be the method by which physicians document medical procedures. Physicians typically hand-write or dictate their notes at the conclusion of a medical procedure. The notes are sent to a transcriptionist for typing. The transcriptionist creates a typed version of the notes by reading the handwritten notes or by listening to the dictated notes and then typing them by hand. Numerous typing errors may occur because of the transcriptionist's unfamiliarity with the physician's handwriting or because it may be difficult to understand the dictation. If the document is proofread for clarity and a question as to the selection of a transcribed word is raised, then, when the listen-and-type methodology is used, it may be difficult to locate the dictation on a dictation audiotape.

After initial transcription, hardcopy documents are typically returned to and edited by the physician. Final edited documents are then manually filed with a patient's medical records. If other physicians or an insurance company require copies of the records, the physician's secretarial staff could prepare the copies and transmit them, as required. Often a number of documents must be generated based on one patient visit. For example, an attending physician may send a thank you letter to a referring physician, an insurance form is often required to ensure proper billing, and follow-up notes may be required to verify the status of the patient or laboratory test results. Time and labor is required to generate each of these documents.

SUMMARY OF THE INVENTION

The present invention uses voice recognition technology and a voice recognition engine to transcribe dictated notes and may eliminate the need for traditional read-and-type or listen-and-type transcription. Method and apparatus for voice dictation and document production are provided. An embodiment of an apparatus to generate an editable text file from a user's dictation using voice recognition technology may include a computer interface and a computer in communication with the computer interface including a voice recognition engine, a database, and a memory.

An embodiment for a method of entry of dictation into a plurality of documents may include receiving an indication of a selection of a plurality of documents from a list of documents, receiving an indication of a field descriptor of a first field in a document, receiving dictated speech to be entered into the first field, writing transcribed text representative of the dictated speech to the first field, and writing the transcribed text to other fields having the same descriptor in each of the other selected plurality of documents.

An embodiment of a method of generating text, including variable data, from dictation, may include converting dictation to a first string of text, prompting a user for a variable value, converting additional dictation to a second string of text representative of the variable value, and combining the first and second strings of text.

An embodiment of a method of generating a document from dictation may include acquiring data related to a plurality of dictation subjects, populating a database with the acquired data, receiving identification of a first field in a document, the first field to include additional data related to a dictation subject, receiving dictated data related to the first field, generating a first audio portion and a first text portion from dictated data, and storing the first audio portion in an audio file and the first text portion in an editable text file.

BRIEF DESCRIPTION OF THE DRAWINGS

The various features of the invention will best be appreciated by simultaneous reference to the description which follows and the accompanying drawings, wherein like numerals indicate like elements, and in which.

DETAILED DESCRIPTION

Figure 1:
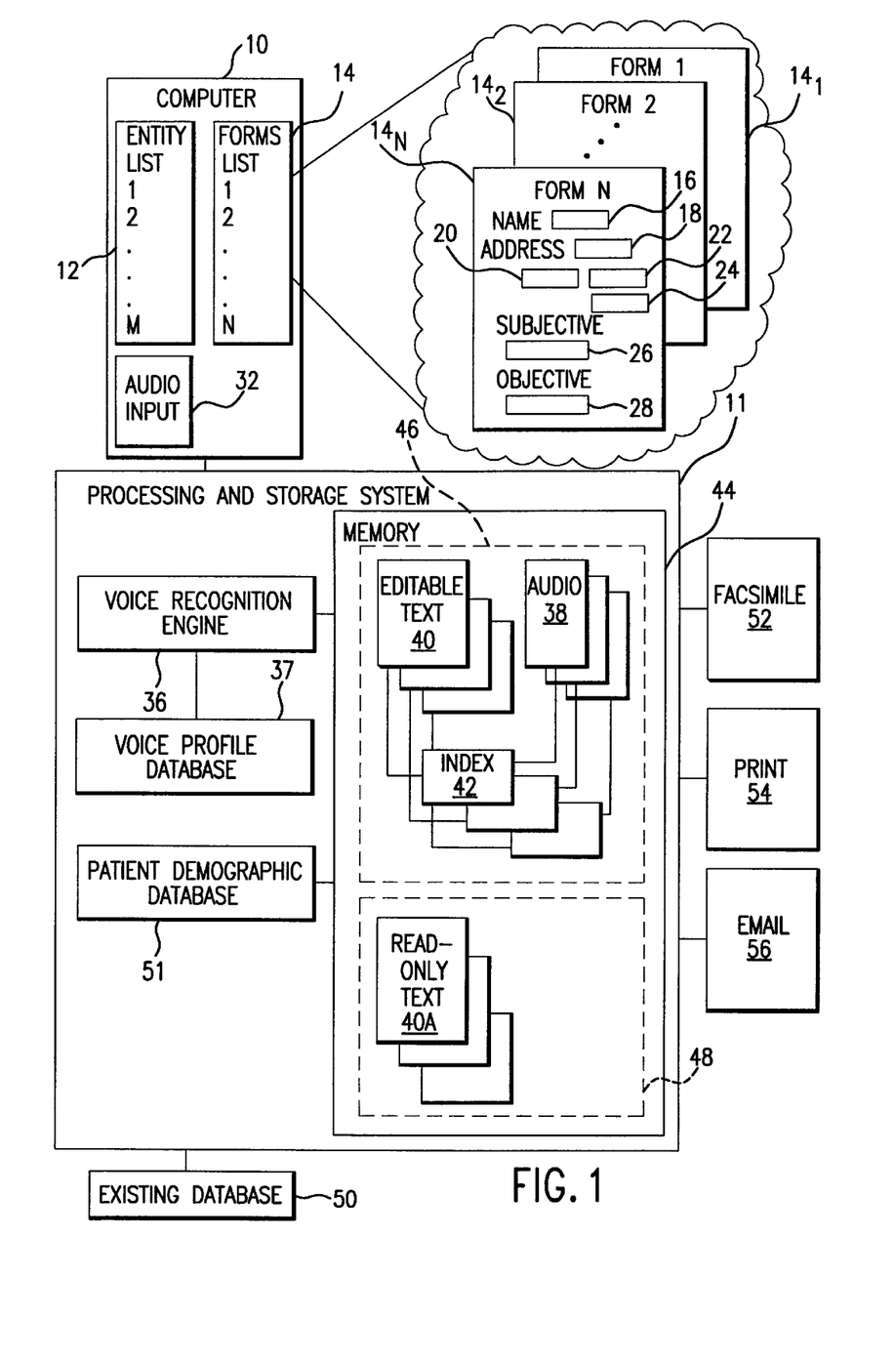
FIG. 1 is a block diagram of an embodiment of the present invention.

FIG. 1 is a block diagram of an embodiment of the present invention. The present invention uses voice recognition technology and a voice recognition engine to transcribe dictated notes and may eliminate the need for traditional read-and-type or listen-and-type transcription. In accordance with an embodiment of the invention, a user may be provided with a personal computer, workstation, or a handheld computing device (collectively referred to as "computer 10"), that may include a monitor, microphone, and pointing device (not shown) such as a mouse, stylus, or keyboard. The computer 10 is operatively coupled to a processing and storage system 11. Using voice commands and/or a pointing device, a user may select the identity of an entity (e.g., a patient or client) that will be the subject of a dictation. The entity therefore becomes the "dictation subject." The entity may be listed on an entity list 12 that may be displayed on a computer 10 monitor. The user may also select a type of document or form (hereinafter "forms") that the user wishes to populate, or fill-in, with text. Selection of forms is not limited to one document; multiple documents can be selected for sequential or simultaneous data entry and processing during one dictation session. The forms may be listed on a forms list 14 that may be displayed on the computer 10 monitor.

The forms list 14 of FIG. 1 is depicted as having N forms $14_1$–$14_N$, where N is any integer. For ease of illustration, an Nth form 14$_N$ is partially illustrated. Forms are typically divided into sections or fields 16–28. Each field may have its own unique descriptor to identify the field, for example, a descriptor may be "Name," "Address," or any number or letter combination to uniquely identify the field. It will be understood that there is no limit to the number of fields that can be associated with any of the forms in the forms list 14 and that the representation of fields having reference numbers 16–28 is for illustration purposes only. In accordance with one embodiment of the invention, a user may select a first field, for example the "Subjective" field 26, which the user wishes to fill-in. After the selected field is filled-in, the user may verbally or manually (e.g., with a pointing device) command the system to go to another field in the same document or in one of the other previously selected documents.

To fill-in a field, the user may dictate speech into an audio input 32 of the computer 10. The audio input may be a microphone. In an embodiment, the processing and storage system 11 may automatically generate an audio file 38, along with an associated transcribed dictation file 40, and an indexing file 42. Such generation may be accomplished with the use of a voice recognition engine 36. The audio file 38, transcribed dictation file 40, and indexing file 42 are stored in a memory 44, which may be, for example, a hard disk or some other type of random access memory. The transcribed dictation file may be saved as an editable text file (hereinafter "editable transcribed text file 40"). The audio file 38 and editable transcribed text file 40 may be indexed by the indexing file 42, such that each transcribed word of dictation in the editable transcribed text file 40 is referenced to a location, and thus a sound, in the associated audio file 38. Alternatively, the audio file 38 and editable transcribed text file 40 may be indexed by the indexing file 42, such that each transcribed letter of dictation in the editable transcribed text file 40 is referenced to a location, and thus a sound, in the associated audio file 38. Indexing, or tagging, each letter in the editable transcribed text file 40, as opposed to each word, improves playback of the audio file and improves editing capability by providing more granularity to the process.

The process of editing transcribed dictation is improved by enabling an editor to select a questioned word or words (or alternatively letter or letters), from the editable transcribed text file 40 and hear the user's recorded voice associated with that selection. When the text is presented to an editor on a computer screen, the editor can click on the text and hear the user's voice associated with that text. The editor can correct any errors due to the voice recognition engine's 36 interpretation of the voice. The voice model may be updated by editing single words to one or more words or multiple words into a single word. Alternatively, or conjunctively, the model may be updated by editorial manipulation of single letters of text.

Associated with the voice recognition engine 36 is a database of voice profiles 37 for each user. The correction of errors in the voice recognition engine's 36 interpretation of the user's voice may be synchronized with the user's voice profile, thus updating the user's voice profile. Because the user's voice profile has been updated, probability dictates that the error may not occur again. The process of editing improves the user's voice model.

After the processes of dictation and editing are completed, and the text contained in the editable transcribed text file 40 is approved, the file containing the approved text is saved in a read-only format, (the saved file will hereinafter be referred to as "read-only format file 40A") thus, effectively deleting the editable transcribed text file 40 from memory 44. The read-only format file 40A may be signed and stored as an electronic signature. Saving the approved text in a read-only format avoids accidental or deliberate tampering with the approved text. Furthermore, to save storage space in the memory 44, the audio file 38 generated in concert with the editable transcribed text file 40, as well as the associated indexing file 42, may be deleted from the memory 44 after the editable transcribed text file 40 is approved.

Logical storage of the pre-approved editable transcribed text file 40 may be in a first section of memory 46 reserved for editable text, while logical storage of post approved read-only transcribed text file 40A may be in a second section of memory 48 reserved for read-only text. Storage in separate logical memory locations improves the speed for a user to replicate a database at a remote location. The scalability to multiple remote sites may be improved with separate logical storage because a user need only mirror read-only transcribed text files, and may thus avoid the unnecessary copying of large audio files and editable files that may not be required at the remote sites. It will be understood that the editable transcribed text file 40 and the corresponding read-only transcribed text file 40A need not share memory 44 contemporaneously with one another. Additionally, the editable transcribed text file 40 and the read-only transcribed text file 40A may be stored in a common section of memory.

The process of generating documents may be improved by giving the user access to legacy information, such as data pertinent to each entity in the entity list 12. This data may already be stored in an existing database 50 of the user. For example, a user in the medical profession, such as a physician, may have a practice management system in place to handle the financial, administrative, and clinical needs of his practice. The practice management system may have a wealth of demographic information about each patient seen in the physician's practice. The demographic information may be stored in a database format. Each item of data may therefore be available for use by the processing and storage system 11. For example, a physician may have a schedule or roster of patients that will be seen on a given day. Each patient may be listed in the physician's practice management system database 50 (i.e., the existing database 50). In accordance with an embodiment of the invention, patient demographic data, for patients to be seen on the given day, may be downloaded from the practice management system database 50 to a patient demographic database 51 before the physician sees the patient. When the physician is ready to prepare notes or complete forms based on the patient's visit on a particular day, the physician may identify the patient to the processing and storage system 11 by use of the entity list 12. Entity list 12 is illustrated with M entities, where M is an integer. An embodiment of the invention may accommodate any number of entities; however, it is noted that the number of entities represented in the database 50 need not be equal to the number of entities listed on the entity list 12. As the entities are selected from the entity list 12, they may be removed from the list 12 to show that the entity has been addressed. This gives a visual reference to the user as to what work has and has not been completed. For example, if a patient's name is selected from the entity list 12, the name is removed from the entity list 12 after the physician dictates his notes. This indicates to the physician that he has dictated a note for that particular visit of that patient. If at the end of the day the physician has an empty entity list 12, then he may understand that he has completed all required dictation. If there are names left on the entity list 12, then the physician may understand that he may be required to complete further dictation.

The physician may select the form(s) that will be completed from the forms list 14. The processing and storage system 11 may automatically fill-in fields, for example fields 16–28, for which data is available, from the downloaded practice management system database 50 or data added directly into the patient demographic database 51. Downloaded information may include patient name, address, telephone number, insurance company, known allergies, etc., but, of course, is not limited to these items.

An embodiment of the invention may dynamically generate and distribute forms, reports, chart notes, or the like based on the entered dictation. Such documents may be placed in electronic archival storage within the user's own control and additionally the processing and storage system 11 may automatically send copies of these documents to third parties. As used herein, the term "documents" includes both electronic and hard copies. Using the medical practice as an example, a physician may dictate chart notes (i.e., a summary of the results of a patient visit) into the processing and storage system 11 via the computer 10. Because dictated information is entered into predefined fields, the processing and storage system 11 may integrate the dictated information into an electronic medical chart that can be archived, retrieved, and searched. Forms, reports, charts, or the like can be sent to third parties via any communication channels, such as fax 52, print 54, and e-mail 56.

Figure 2:
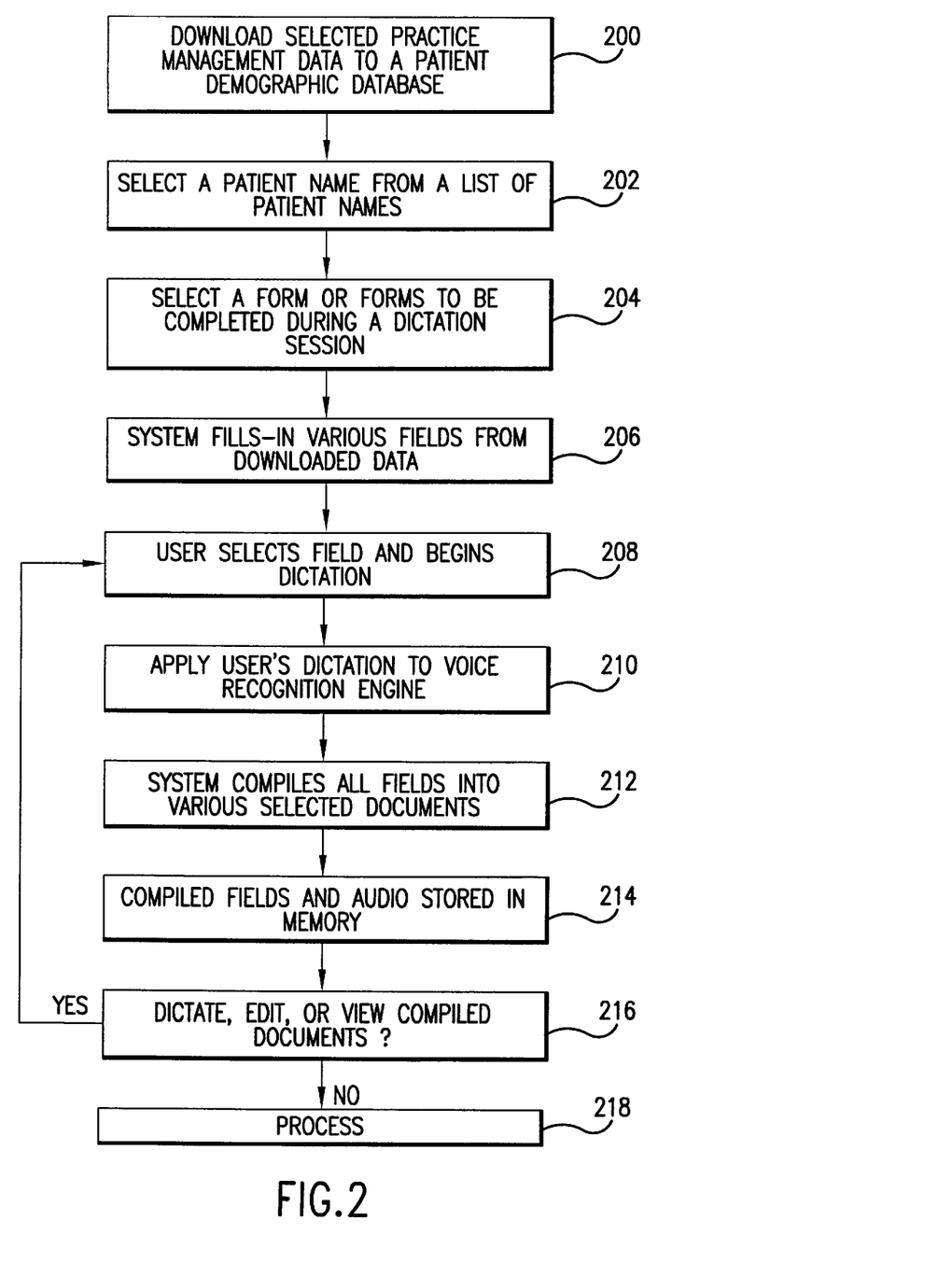
FIG. 2 is a flow diagram illustrating a method of operation in accordance with an embodiment of the invention.

FIG. 2 is a flow diagram illustrating a method of operation in accordance with an embodiment of the invention. The method of operation is illustrated in the context of a medical practice; however, it will be understood by those of skill in the art that the method is equally applicable to other services and industries as well. At step 200, selected data from database 50 holding information relating to patient practice management database 51 is downloaded to a patient demographic database. At step 202, a first user, i.e., the physician, may select a patient name from the list of patient names previously downloaded. At step 204, the first user may select the form or forms that will be filled-in during a dictation session. The forms used can be unique to the user's own practice or industry. The system dynamically generates forms by compiling separate fields of data. The user populates each of these fields with text as the user dictates into the system. Fields can also be populated by omission with preformatted form defaults. Thus forms, whether new or old, can be compiled by inserting the proper field contents within a text box, check box, or other data entry location in the form.

The use of fields provides a benefit for data-mining of the fields. Data-mining, as used herein, relates to the process of searching a database, or other storage place of data, for particular data or sets of data. The use of separate fields is a benefit because known existing databases for use in dictation generally have data entered in a free-form style. By free-form, it is meant that text is dictated in a free flow format into essentially one data field, as contrasted with text dictation into structured and distinct fields. Free-form dictation results in data storage that is not amenable to document generation or data-mining. Forms customization allows discrete data to be captured and saved.

At step 206, the system may fill-in various fields in any of the forms selected by the first user. Data used by the system to fill-in the forms may come from the patient demographic database 51, which was populated with data downloaded from the first user's own database 50 or from other sources. Because forms are divided into fields, the text in like fields may be shared between different forms and generation of multiple forms may occur contemporaneously. This is an improvement over existing systems, which require a user to fill-in one form at a time. The completion of one form at a time may be driven from a system requirement to engage a voice recognition engine to complete one form and then disengage the voice recognition engine before moving onto the next form. Completion of the dictation session is slowed in that instance, because the user may be duplicating his efforts by filling-in like fields in different forms. In an embodiment of the invention, several forms may be generated in one session, without the need to dictate entries for one form, close that form, then dictate entries for another form. Once all desired forms are identified, the user can populate the fields of each of the forms in one session.

At step 208, the first user may select a first field and begin dictation. In an embodiment of the invention, the first user can use voice navigation to select a field, where voice navigation includes the speaking of the desired field name to effect data entry into that field. Data entry includes all forms of spoken word, including numbers. Any type of data entry may be accommodated, for example, both text boxes and check boxes may be used. Text may be entered into a text box and checkboxes may be checked or unchecked by voice entry. Pointing devices need not be used. Thus, if there are four fields the first user can say "field one" and the text will be entered into field one. The first user can then say "next section" or call the next section by name, such as "field two." Of course fields can be named with common names such as "subjective" or "allergies," and need not be numbered. Additionally, after the user indicates to the system that dictation is about to begin, the system provides a visual and/or audible cue to the user to allow the user to understand that the system is ready to accept dictation. In one embodiment, the background of a dictation screen on the computer monitor turns yellow so that the user can easily tell if the voice recognition engine is engaged. When the command "stop dictation" is issued, the background of the dictation screen returns to its original, pre-dictation, color. This also enables the user to see what state the system is in, even if the user is standing or pacing while dictating several feet away from the workstation. In addition to the screen changing color when dictation is initialized and terminated, one embodiment emits an audible tone so that the user does not have to look at the computer screen during dictation. The combination of yellow screen and audible tone makes it clear to the user when the voice recognition engine is starting and stopping, thus avoiding any unnecessary repetition of dictation. Each of these features can be disengaged if not desired by the user.

At step 210, the first user's dictation is applied to a voice recognition engine. The output of the voice recognition engine populates fields with like-names in different documents. There is no need to disengage the voice recognition engine in order to dictate a second form. For example, a patient may come to a physician's office for an examination. The physician may use an embodiment of the present invention to document the encounter. The physician may choose a familiar form in which to enter data and can dictate data directly into that form. The physician may also need to generate a request for laboratory work to be performed at a testing laboratory, a follow-up note to the patient, and a thank you letter to the referring physician. Each of these multiple documents may have some fields that are identical to the fields used to record the encounter with the patient, for example "name" and "address." In accordance with an embodiment of the invention, the system can populate the multiple documents at substantially the same time that the system populates the first document chosen by the physician.

At step 212, once the dictation session is complete, the system may compile all fields into the selected form(s), and thus generate the selected document(s). Because transcribed information is stored in fields, rather than actual assembled documents, a user may create numerous documents by assembling or merging the appropriate fields into a form represented by a document listed on the forms list 14 (FIG. 1). The assembled fields may then be presented as a completed document.

As the user dictates speech, the user may wish to perform a verbal abbreviation for certain words, phrases, sentences or entire paragraphs of text that are often repetitive in the course of the user's generation of documents. To allow such abbreviation, the system may allow the user to recite a sound known by the system to represent a certain string of text. Such an abbreviated dictation tool is known as a "macro." In the medical industry, for example, frequently used phrases are called "norms" or normals, and can be completed by the use of a macro. When the system encounters a macro, it substitutes the string of text corresponding to the macro into the text file that is generated by the voice recognition engine. The method of inserting a macro into a string of words in a text file may include: correlating the string of words against entries in a database of command strings; copying, upon identity of correlation, the macro at a pointer address of the command string; and replacing the correlated string of words with the copied macro. The user may indicate to the system that the user's next word will be a macro. In an embodiment of the invention, the user may indicate that the next word is a macro by saying the word "sub" followed by the name of the macro. Thus, a physician may say "sub thanks" and the system may generate the following: "Thank you for referring the above-identified patient to our offices." The use of norms in the medical services field is well known; however, an embodiment of the invention allows for the use of what are referred to by the inventors as "variable macros" and "prompted macros."

A variable macro combines a macro with a data variable retrieved from a database. Thus, a user may say "sub thanks" and the system may generate the following: "Thank you for referring [PATIENT NAME] to our offices." Where [PATIENT NAME] is a data field and the instance of [PATIENT NAME] to be substituted in the example above would be defined by the selection of an entity from the entity list 12 at the beginning of the dictation session. Thus, if the entity were named "John Brown" the actual text generated by the system would be: "Thank you for referring John Brown to our offices."

A prompted macro allows a user to generate text that requires the insertion of variables that may not be present in the patient demographic database 51. In an embodiment, the prompted macro is used as follows. The physician says "sub macro_name," waits for a prompt from the system such as a beep, and then says or enters the variable data. Thus, as an example, if a patient had taken a lead blood level test and the result of 5 deciliters/liter was returned to the physician, the physician may say "sub high lead," wait for a beep, and then say "five." The system in turn may generate the following text: "The results of your lead blood screening indicate a level of 5 deciliters/liter. This level is higher than would normally be expected." Thus, the variable "5" was inserted into an appropriate spot in the text of the macro.

At step 214, the compiled fields and audio may be stored in memory. At step 216, the user may dictate, edit, or view the compiled documents. If further dictation, editing, or viewing is required, the first user may return to step 208. The first user or a second user may edit the document. Authorization of the second user may be required. The second user may edit from any workstation or other input/output device associated with system. Additionally, any editing that the second user performs may update the first user's voice model. This may be important in improving accuracy. Any person with authorization may view the documents on a workstation in communication with the processing and storage system. If further dictation, editing, or viewing of compiled documents is not desired, then at step 218 further processing of the documents may occur. Further processing may include, but is not limited to: secure storage of transcribed text files in a read-only format; creation of electronic medical records ("EMRs") or charts that logically combine information for a patient; creation of voice enabled EMRs; display of documents on a monitor; faxing; printing; or e-mailing documents using pre-defined settings. Automated transmission of any document to a pre-defined recipient is accommodated in one embodiment in accordance with the invention. Each created document may be appended to its corresponding patient's electronic patient chart, eliminating any need for cutting and pasting found in some other applications. A search function allows users to retrieve documents using a variety of search options such as keyword, date, patient name, or document type.

Figure 3:
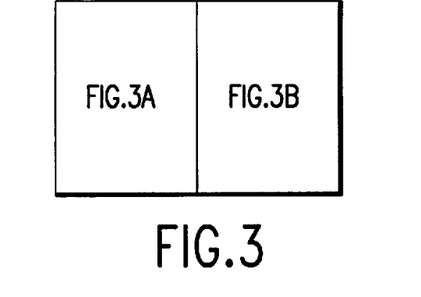
FIG. 3 illustrates various components of a system in accordance with an embodiment of the invention.
Figure 3A:
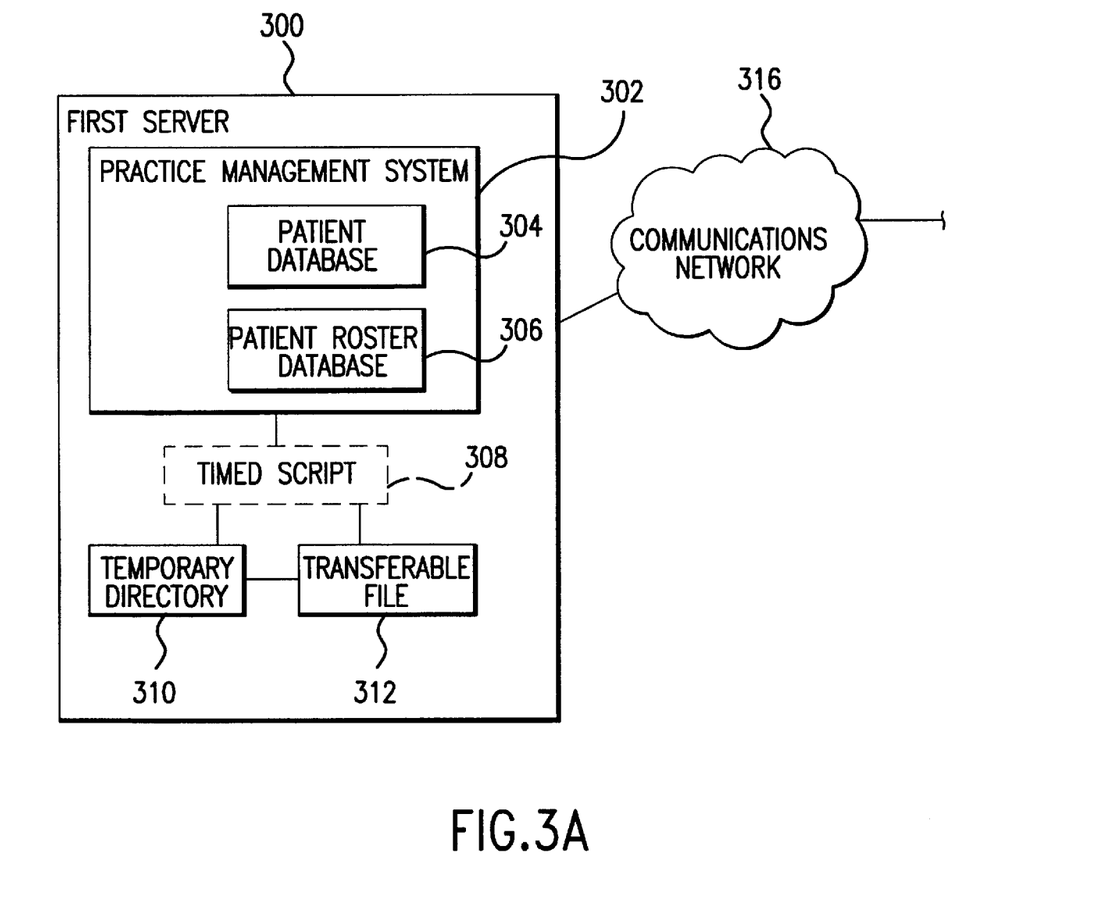
Figure 3B:
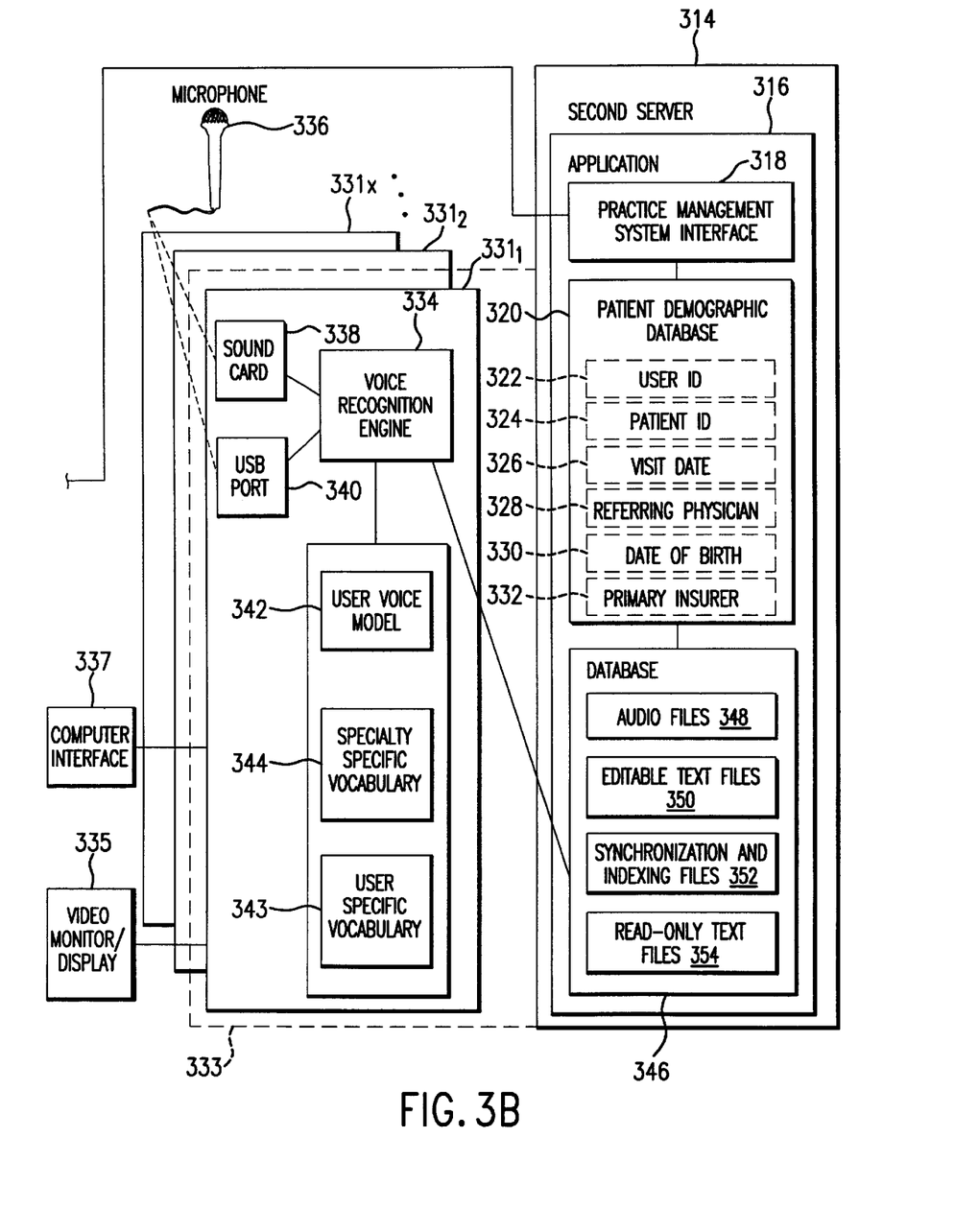

FIG. 3 illustrates various components of a system in accordance with an embodiment of the invention. A first server 300 includes a practice management system 302. The practice management system 302 may be a third party system used for entry, storage, and processing of patient demographic data. Patient demographic data may be stored in a patient database 304. Patient demographic data includes information having, but not limited to, such field headings as: date of birth, primary insurer, employer, social security number, and address, visit date, and referring physician. Patient demographic databases may include hundreds of fields of information for each identified patient. The practice management system 302 may process this information to generate, for example, patient bills and patient reports. Examples of practice management systems 302 that may be used in accordance with an embodiment of the invention are The Medical Manager™ by WebMD and Lytec™ by NDC Medical. These are examples in the medical industry, but the invention would operate similarly with informational databases in other industries as well.

Data stored in the patient database 304 may be in a number of formats including, but not limited to, Access, SQL, MSDE, UNIX, and DOS. The practice management system 302 may also include a patient schedule or roster database 306. The patient roster database 306 includes information indicative of which patient will be seen on a given day.

In an embodiment of the invention, a timed script 308 or real-time interface (not shown) may be used to query the patient roster database 306 to determine which patients will be seen on a given day. The timed script 308 may then effectuate a download of patient demographic data of the patients to be seen on the given day. It may also download patient demographic data that may heave been updated since a previous download. The download of patient demographic data from the patient database 304 may be to a temporary directory 310 on the first server 300. In an embodiment of the invention, the timed script 308, which may be a length of computer code that performs an action on a timed interval, logs into the practice management system 302 as a user. The timed script 308 may generate a specific report, such as a demographic download for the patients designated to be seen on the next day by the patient roster database 306.

It will be understood, however, that the timed script 308 can retrieve data for any period of time, and for any possible patient selection criteria. The download may be written to the temporary directory 310 on the first server 300. One of skill in the art will recognize that different methodologies may be used to download patient demographic data without departing from the scope of the invention. Downloading methodologies may depend, in part, on the particular practice management system 302 in use and may also be completed in "real-time."

The timed script 308 may also facilitate the parsing of downloaded data. For example, the patient database 304 may have twenty tables and five hundred fields. The timed script 308 may be used to extract just the data required to be operated upon by an embodiment of the invention from a subset of these fields, for example seventy-five out of the five hundred fields. The timed script 308 may also generate a transferable file 312. The transferable file 312 may then be transferred to a second server 314.

The second server 314 may be coupled to the first server 300 by a communications network 316. The communications network 316 may be a public switched telephone network, an intranet, the Internet, or any other communications network, or any combination of data-bearing networks suitable to couple the respective servers 300, 314 to allow communication and data transfer to be performed therebetween. While two servers are shown, the methods and apparatus described herein can be performed equally well by sharing one server, or by sharing two or more servers.

In accordance with an embodiment of the invention, the second server 314 includes an application 316 to operate on data included in the transferable file 312. The data included within the transferable file 312 includes data stored in the temporary directory 310 of the first server 300. The application 316 includes a practice management systems interface 318 and a patient demographic database 320. The practice management systems interface 318 parses the data included in the transferable file 312, which is transmitted from the first server 300 to the second server 314 via the communications network 316. The practice management systems interface 318 parses and maps the data such that the data can be indexed and entered into the appropriate locations in the second server's 314 patient demographic database 320. Mapping may be necessary because the field names in the patient database 304 of the first server 300 may not necessarily match the field names used in the patient demographic database 320 of the second server 314. The practice management system interface 318 may therefore be used to map data from a field having a first heading into a field having a second heading. The practice management system interface 318 provides versatility to the embodiment of the invention by allowing the invention to interface with a plurality of practice management systems.

There may be an unlimited number of fields within the patient demographic database 320. The fields may be used for storage of indexed data from any practice management system provided the appropriate mapping is performed by the practice management system interface 318. In one embodiment, more than seventy-five fields are used. Exemplary fields may include user ID 322, which defines a voice model to use for voice-to-text conversion for a given voice recognition engine; patient ID 324, which may include the patient's social security number or other unique identification number; visit date 326, which may include the date the patient saw the physician; referring physician 328, which may include the name, address, phone number and/or other indicia of a physician that referred the patient to the attending physician; date of birth 330; and primary insurer 332, which are self-explanatory, and other fields. Data may also be added manually into fields.

The second server 314 may also include a voice recognition engine 334, such as the runtime portion of ViaVoice™ manufactured by IBM. Typically a voice recognition engine is separable into at least two parts: 1) runtime software to perform voice-to-text translation and manage dictated speech in a .WAV file, and 2) administrative software to generate screens and help files and provide the ability to correct translated text. Other voice recognition engines and runtime software may be used without departing from the scope of the invention. An embodiment of the invention may use open-architecture, with respect to the voice recognition engine, so as new voice recognition technologies are developed they can be integrated into the invention.

The voice recognition engine 334 may receive voice input (i.e., dictation) via a coupling to a noise-canceling microphone 336. Noise-canceling microphones are available in many different styles, such as handheld, tabletop, and headset integrated. The function of a noise-canceling microphone 336 is to help eliminate background noise that may interfere with the accuracy of the voice recognition engine's 334 speech-to-text function (i.e., transcription of spoken words into textual words). The particular noise-canceling microphone 336 used may depend upon the recommendation of the manufacturer of the voice recognition engine 334. In one embodiment, a model ANC 700 noise-canceling microphone manufactured by Andrea Corporation is used. Some noise-canceling microphones 336 are coupled to the voice recognition engine 334 via a sound card 338. Still other voice recognition engines may receive voice input from a noise-canceling microphone coupled to a Universal Serial Bus ("USB") port 340 on the server.

The voice recognition engine 334 may use user voice models 342, user specific vocabularies 343, and specialty specific vocabularies 344 to effect the transcription of voice-to-text. The user voice models 342, user specific vocabularies 343, and specialty specific vocabularies 344 may be stored in the memory of the second server 314. Models and vocabularies may be selected based on User ID 322. User ID 322 may come from the physician dictating speech into the noise-canceling microphone 336. The physician may enter identification information into the system by means of a computer interface 337, such as a keyboard or other data entry device before dictating his or her spoken words. Verification of entered data may be accomplished in real time by observation of a computer video monitor/display 335.

The specialty specific vocabulary 344 may be a database of sounds/words that are specific to a given specialty, such as law or medicine. Using medicine as an example, the single word "endometriosis" may be transcribed as the group of words "end 'o me tree 'o sis" by a voice recognition engine not augmented by a specialty specific vocabulary 344. Additionally, correction may allow words to be automatically added to a user's vocabulary. The user specific vocabulary 343 may allow users to add words that may not be in a specialty specific vocabulary 344.

The voice recognition engine 334, user voice model 342, user specific vocabularies 343, specialty specific vocabulary 344, sound card 338, and USB port 340 may all be included in a computer workstation of personal computer $331_1$ that is physically separated from, though still in communication with, the second server 314. Multiple workstations, in a networked computer system, represented by reference numbers $331_2$–$331_X$, where X is any integer, may access the second server 314. The multiple workstations $333_1$–$333_X$ need not be identical. Alternatively, the voice recognition engine 334, user voice model 342, user specific vocabularies 343, specialty specific vocabulary 344, macros and templates 345, sound card 338, and USB port 340, represented as being included in workstation $331_1$, may all be included in the second server 314, as illustrated by the dashed line labeled 333 in FIG. 3. All voice models may reside on the second server 314 and be moved to each user when the user logs on. The models can be copied back to the second server if, for example, a voice model changes during that session.

The output of the voice recognition engine 334 may be applied to a database 346 that stores text files and associated other files related to a dictation session. The format of the database 346 may be, for example, Access™ by Microsoft, SQL Server™ by Sybase or Microsoft Data Engine (MSDE™) by Microsoft. Other formats may be used without departing from the scope of the invention.

Files may be logically stored in the database 346 based on, for example, whether they are stored awaiting editing or stored for archival purposes. Regarding files stored for editing, at least three types of files may be stored: 1) an audio file 348 that is generated by the voice recognition engine 334 as a user dictates; 2) a corresponding editable text file 350 that was either generated concurrently with the audio file, was generated by running the audio file through a voice recognition engine 334, or may have been typed in; and 3) a synchronization and indexing file 352 that synchronizes and indexes the sounds in the audio file 348 to the text in the editable text file 350. The audio file 348 may be in .WAV format, other formats may also be used. The editable text file 350 may remain in an editable format throughout any processing of the files that may be required. Processing may include any number of cycles of editing, review, and approval. At the conclusion of processing, the data in the editable text file 350 may be stored in a read-only format (referred to hereinafter as read-only text file 354. Read-only text files 354 are stored without an association to an audio file or a corresponding synchronization and indexing file. In an embodiment of the invention, the audio file 348, editable text file 350, and synchronization and indexing file 352 used to prepare the read-only text file 354 are deleted from memory 346 once the read-only text file 354 is approved. One purpose of deleting the files used to prepare the read-only text file 354 is to reduce storage space required on the second server 314 or other data storage device (not shown) used to store such data. Another purpose of deleting the files used to prepare the read-only text file 354 is to prevent tampering or accidental alteration of the stored documents. A read-only text file 354 may be signed and stored as an electronic signature.

Figure 4:
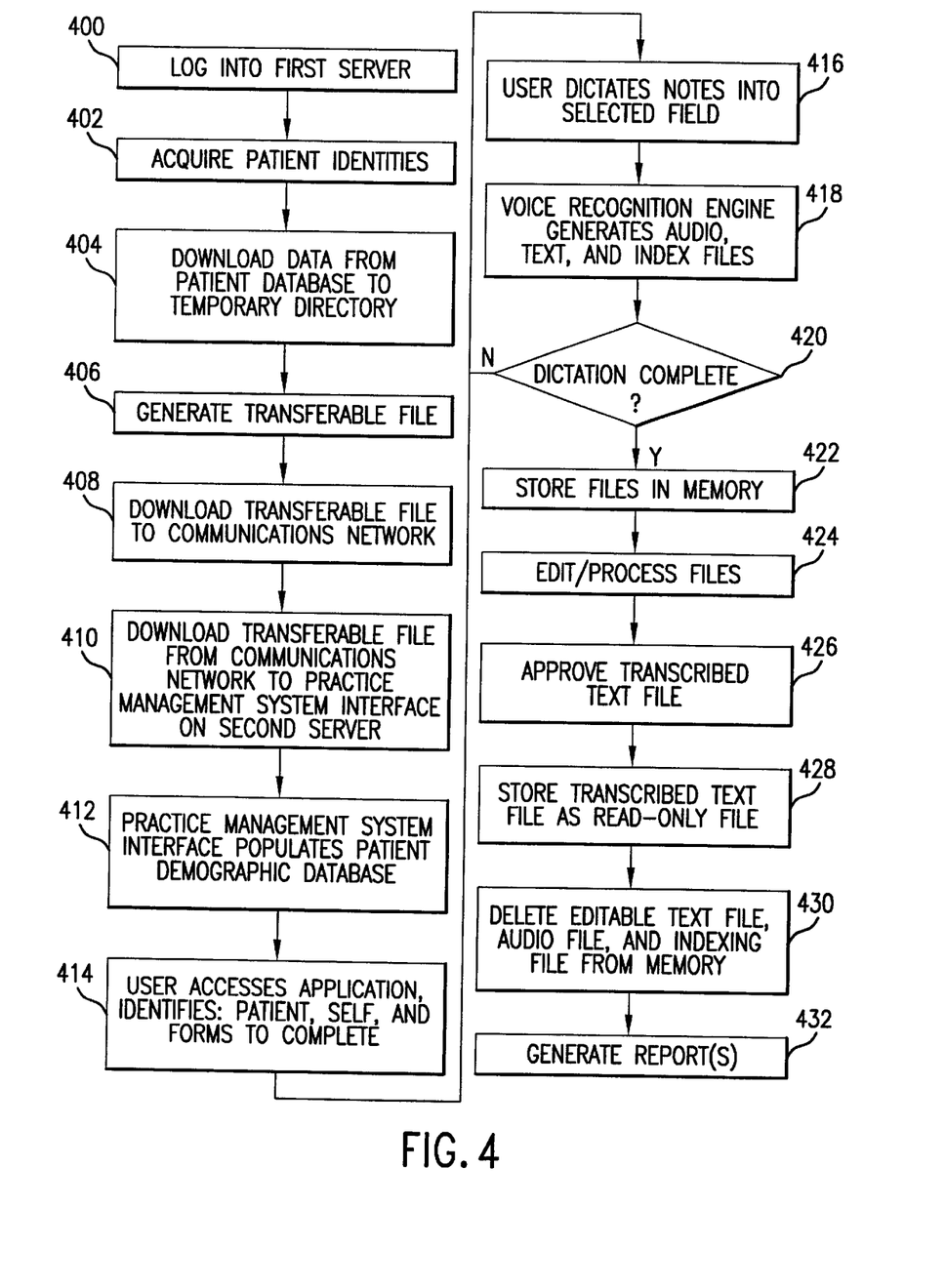
FIG. 4 is a flow diagram illustrating another method of operation in accordance with an embodiment of the invention.

FIG. 4 is a flow diagram illustrating another method of operation in accordance with an embodiment of the invention. The method of operation is exemplified by a method with which a physician may use the embodiment of the invention; however, it will be understood that the method may be used in any field of endeavor. The reference numbers of FIG. 3 will be used as an aid in the description of the method of operation in accordance with FIG. 4, however use of these reference numbers will not constrain the method of operation to the embodiment of FIG. 3. One method for transferring data is a timed script. Other methods include a real-time pull of data from a database and pull of data on demand from a database. In a pull on demand, the system may retrieve information related just to one dictation subject (i. e., one entity) or many dictation subjects. At step 400, a timed script 308 on a first server 300 logs into the first server 300. At step 402, the timed script 308 acquires the identities of patients to be seen by a physician on a given day. At step 404, the timed script 308 downloads data from a patient database 304 to a temporary directory 310. At step 406, the timed script 308 generates a transferable file 312 using data downloaded to the temporary directory 310. At step 408, the timed script 308 downloads the transferable file 312 to a communication network 316 for transfer to a second server 314. At step 410 the transferable file 312 is downloaded from the communications network 316 to the practice management system interface 318 included in an application 316 included in the second server 314. At step 412, a practice management system interface 318 populates a patient demographic database 320 with data mapped from the transferable file 312. At step 414, a user (e.g., a physician) accesses the application 316 via a computer interface 337. As part of the access procedure, the physician may indicate his or her identity (e.g., User ID 322) to the application, so that the application is able to associate the physician's User ID with the physician's voice model (e.g., a voice model stored in user voice model file 342). As part of the access procedure, the physician may also indicate a patient ID (e.g., Patient ID 324), so that the application will be able to associate the patient's ID with patient data downloaded from the first server 300 in the transferable file 312. As part of the access procedure, the physician may also indicate which form types the physician will be using to structure his dictation. Form types may be stored in the memory of the second server 314. Access to the application and indication User ID and Patient ID may be made by voice using a noise-cancellation microphone 336 or manual manipulation of a computer interface 337. Verification of entries is accomplished in real time by observation of a computer video monitor/display 335. At step 416, the physician may dictate a report to the application 316 by speaking into the noise-cancellation microphone 336. The report may be structured in accordance with the form the physician has selected for initial data input. By structure, it is meant that the report may be broken down into a plurality of fields, each field having associated therewith a filed name. The first user indicates to the application into which field the user will enter dictation. Dictation (i. e., speech) received by the noise-cancellation microphone 336 is converted to electrical signals and applied to the voice recognition engine 334. At step 418, the voice recognition engine 334 substantially simultaneously generates an audio file 348 corresponding to the dictated speech, transcribes the dictated speech into an editable text file 350, and generates a synchronization and indexing file 352. The audio file 348 may be in .WAV format, other formats may also be used. The synchronization and indexing file 352 associates each transcribed word of text in the editable text file 350 with a sound in the audio file 348. At step 420, the physician indicates to the application that entry of dictation in the first field is complete or that the dictation session is at an end. If dictation is not complete or the dictation session is not at an end, the user may return to step 416. The indications may be explicit, as when the user indicates that dictation in the field is complete, or it may be implicit, as when the user indicates that dictation should commence in the next field. Such an implicit indication may be in the form of the utterance of the words "next section." Additionally, the application 316 may recognize that data input to a field is complete, as in the case of a checkbox field, where once a box is checked or not checked no further data entry is feasible. In any case, once the dictation session is complete, at step 422, the application stores the audio file 348, the editable text file 350, and the synchronization and indexing file 352 in the second server 314. At step 424, the editable text file 350 is edited/processed, with or without the use of the audio file 348 and synchronization and indexing 352 file. Editing/processing may occur immediately or may be deferred. Even if a note is deferred, a user may return to the note and dictate or otherwise add to the deferred file (note.) At step 426, the content of the editable text file 350 is approved. At step 428, the editable text file 350 is saved in a read-only format. For ease of description, the editable text file 350, which has been saved in a read-only format, will hereinafter be referred to a read-only text file 354. At step 430, the editable text file 350, audio file 348, and synchronization and indexing file 352 that resulted in the generation of the read-only text file 354 are deleted from the second server 314. Storing the approved dictated form as a read-only text file 354 prevents persons or automated processes from tampering with the file. Furthermore, deleting the editable text file 350 and its associated audio file 348, and synchronization and indexing file 352 from the system provides additional storage space for new files. At step 432, the application 316 may generate output, such as reports, faxes, and/or emails, by compiling fields previously saved as read-only text files 354.

Figure 5:
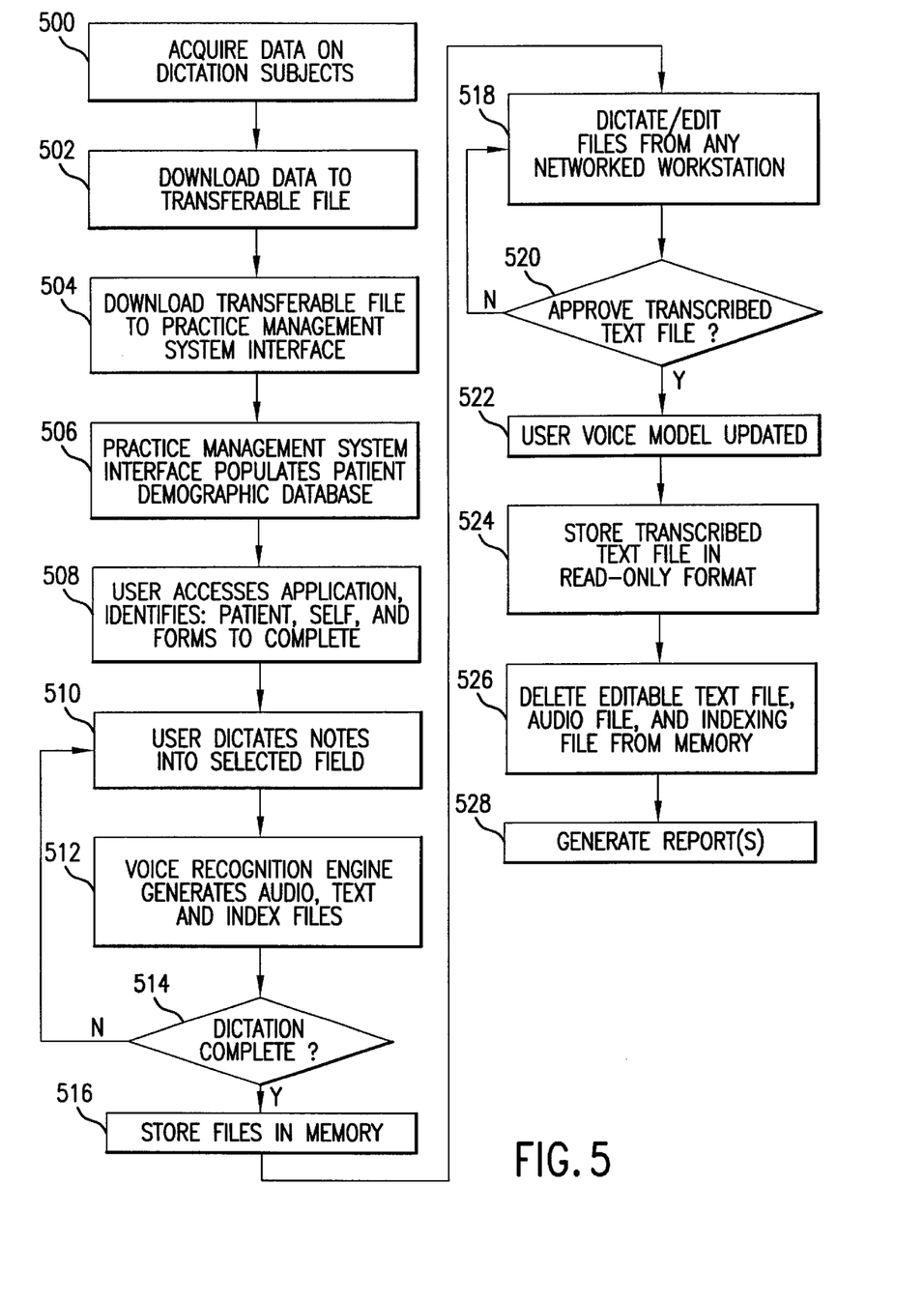
FIG. 5 is a flow diagram illustrating an alternate method of operation in accordance with an embodiment of the invention.

FIG. 5 is a flow diagram illustrating an alternate method of operation in accordance with an embodiment of the invention. At step 500, the system acquires data on dictation subjects from a source, such as, for example, a first server. Data acquisition may be by any manner known to those of ordinary skill. One method of transferring data may be by timed script. Other methods include a real-time transfer of data and a transfer of data on demand. At step 502, acquired data may be downloaded from the source to transferable file. At step 504, the transferable file may be downloaded to a server upon which is located an interface for data processing. At step 506 the interface populates a Dictation Subject Demographic Database with data mapped from the transferable file. At step 508, a user (e.g., a physician or any network user) accesses the application via a computer interface. The computer interface may be one node in a plurality of nodes of a networked computer system. As part of the access procedure, the physician may indicate his or her identity to the application, so that the application would be able to associate the user's identity with the user's voice model. As part of the access procedure, the user may also indicate a Dictation Subject identity, so that the application would be able to associate the Dictation Subject's identity with the Dictation Subject data downloaded from the source and included in the Dictation Subject Demographic Database. As part of the access procedure, the physician may also indicate which form types the user will be using to structure his dictation. Access to the application and indication User ID and Patient ID may be made by voice using a noise-cancellation microphone or manual manipulation of a computer interface. Verification of entries is accomplished in real time by observation of a computer video monitor or by audible cues provided by the application. At step 510, the user may dictate notes into selected fields in the form or forms chosen by the user. Each form may be broken down into a plurality of fields, each field having associated therewith a filed name. At step 512, a voice recognition engine receives the dictation and substantially simultaneously generates an audio file corresponding to the dictated speech, transcribes the dictated speech into an editable text file, and generates a synchronization and indexing file. The audio file may be in .WAV format, other formats may also be used. The synchronization and indexing file associates each transcribed word of text in the editable text file with a sound in the audio file. At step 514, if dictation is not complete, the user may add text into selected fields by returning to the step of dictating notes into selected fields, step 510. If, at step 514, the dictation is complete then, at step 516, the application stores the audio file, the editable text file, and the synchronization and indexing file in a memory. The memory may be on a server in the networked computer system. At step 518, the editable text file may be edited/processed, with or without the use of the audio file and synchronization and indexing file. Editing/processing may occur immediately or may be deferred. Even if a note is deferred, a user may return to the note and dictate or otherwise add to the deferred file (note.) At step 518, the user, or any other authorized user from any computer or workstation in the networked computer system can recall the saved editable text file document or form and add dictation or edit the document or form. In an embodiment, free-form dictation may be limited to the user, while any other authorized user may be limited to dictating corrections. At step 520, if the editable text file is approved, then at step 522 the user's voice model is updated. At step 524, the editable text file is saved in a read-only format. For ease of description, the editable text file, which has been saved in a read-only format, will hereinafter be referred to a read-only text file. At step 526, the editable text file, audio file, and synchronization and indexing file are deleted from memory. Storing the approved dictated form as a read-only text file prevents persons or automated processes from tampering with the file. Furthermore, deleting the editable text file and its associated audio file, and synchronization and indexing file from the system provides additional storage space for new files. At step 528, the application may generate reports, faxes, and/or emails by compiling fields previously saved as read-only text files.

Figure 6:
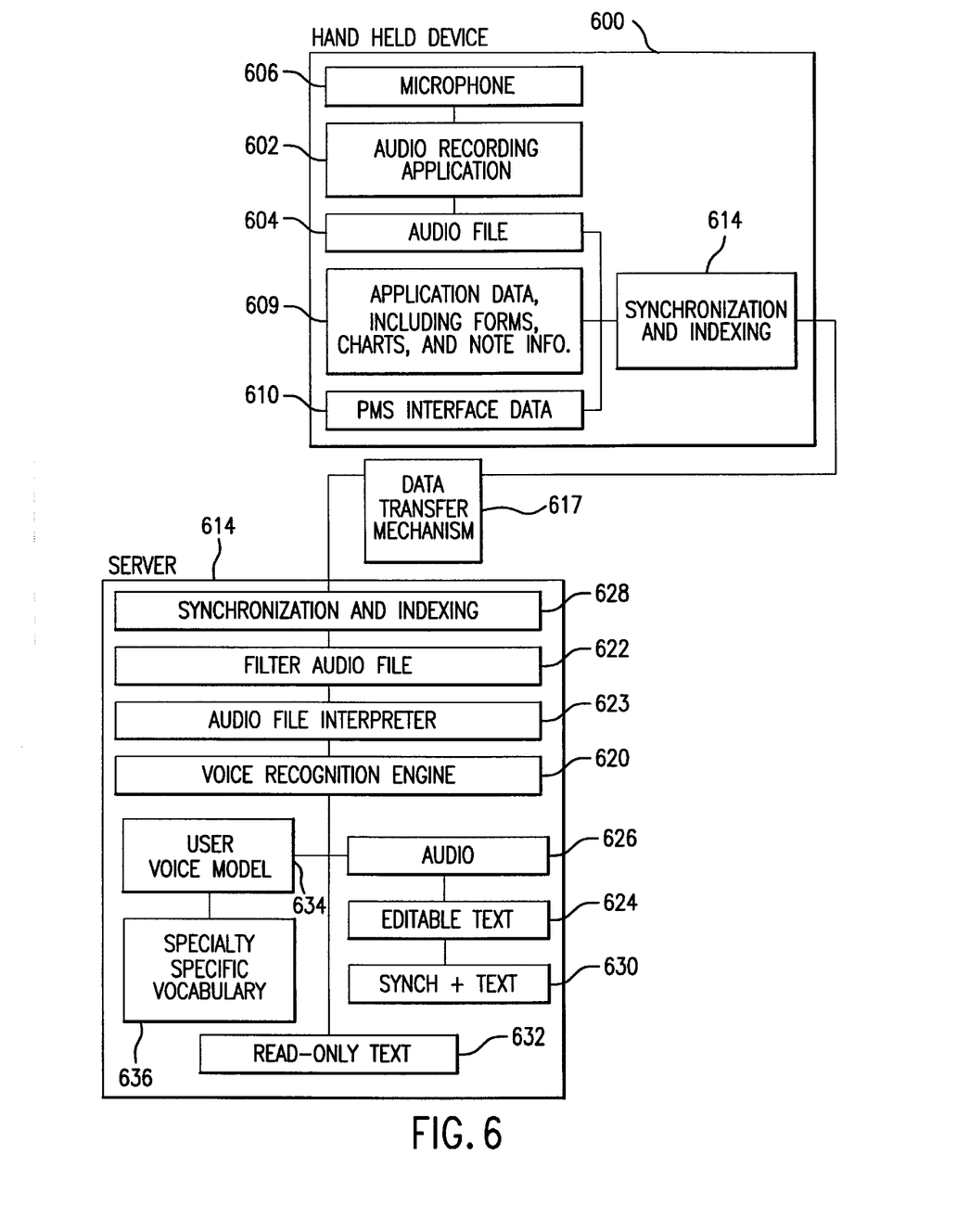
FIG. 6 depicts another embodiment in accordance with the invention.

FIG. 6 depicts another embodiment in accordance with the invention. In the embodiment of FIG. 6, a handheld computing device 600, such as a Cassiopeia® by Casio, a Jornada™ by Hewlett-Packard, or an IPAQ™ by Compaq, using a Windows CE™ operating system from Microsoft Corp., may be used to record initial dictation. Other operating systems, such as the Palm™ Operating System by 3COM, Inc. may alternatively be used so long as they support an audio recording capability. In one embodiment, the handheld computing device 600 runs an audio recording application 602 at a sampling rate of 11 kHz that generates a .WAV formatted audio file 604. Of course, other sampling rates and formats of audio files are acceptable without departing from the scope of the invention. The audio file 604 is generated as dictation is entered into the handheld computing device 600. Dictation may be entered into the handheld computing device 600 via a microphone 606 in communication with the handheld computing device 600.

The handheld computing device 600 may acquire data from a server 614 via a data transfer mechanism 617. The data transfer mechanism 617 may include, for example, a modem, a LAN (local area network) interface, an Internet connection, wireless interconnection including radio waves or light waves such as infrared waves, removable data storage device, or hard wired serial or parallel link.

In the exemplary embodiment of FIG. 6, the data transfer mechanism 617 may be a removable data storage device, such as a CompactFlash™ memory card by Pretec Electronics Corp. In one embodiment, the removable data storage device has a storage capacity size of 64 megabytes. The size of removable data storage device is related to the amount of dictation and data a user desires to store on the card; other sizes may be used without departing from the scope of the invention. The removable data storage device may be removed from the handheld computing device 600 and placed into a data storage device reader (not shown) such as the USB CompactFlash™ card reader by Pretec Electronics Corp. The data storage device reader can transfer data from the removable data storage device to the server 614 or can transfer data from the server 614 to the removable data storage device.

In the example of a medical practice, data acquired by the handheld computing device 600 from the server 614 via the data transfer mechanism 617 may include data from a practice management system, which has demographic data on each patient seen in the practice. Patient demographic data and scheduled patient information, for example, may be collected in the same manner as described in the text related to FIGS. 3, 4, and 5. Patient demographic data, perhaps in the form of a transferable file such as transferable file 312 (FIG. 3) may be input to the handheld computing device 600 and stored in a practice management system interface database 610.

The amount of patient demographic data downloadable to the handheld computing device 600 and the amount of functionality that may be incorporated into the handheld computing device, may be limited by the memory and storage capacity of the handheld computing device 600. As the memory and storage capacity of handheld computing devices increase, the amount of data and functionality incorporated within the handheld device should commensurately increase. Nothing herein should be construed as to limit the types or amounts of data, or to restrict any of the various functionalities of the invention disclosed herein, from being incorporated to the greatest extent possible into a handheld computing device.

Patient demographic data may be used to organize information on the handheld computing device 600. The information downloaded may include demographic data as well as past dictated notes. In addition, the handheld computing device 600 may import application data 609, such as, but not limited to, forms, charts, and note information. The handheld computing device's 600 practice management system interface database 610 may be in the format of Access™ by Microsoft or Sequel Server™ by Sybase. Other database formats are also acceptable and using a different database will not depart from the scope of the invention.

The application data 609 and data stored in the practice management system interface database 610 are synchronized on the handheld computing device 600 by a synchronization and indexing routine 612. The synchronization and indexing routine 612 on the handheld device 600 cooperates with a counterpart synchronization and indexing routine 628 on the server 614. Synchronization in this context refers to downloading of demographic information and application data such as forms, charts, and note information from the server 614 to the handheld computing device 600, and the transfer of audio files and data to the server 614 from the handheld device 600. Once data is downloaded and synchronized on the handheld device 600 the synchronized data is available for document creation and dictation. A dictated audio file 604, will be associated with the form selections made by the user. Other pieces of information, as entered by a stylus, check box, or other method, are also associated with the form selection. The synchronized audio file 604, application data 609, and data from the practice management system interface database 610 may be prepared for transfer via the data transfer mechanism 617.

Synchronized and indexed data transferred from the handheld device 600 to the server 614 via the data transfer mechanism 617 may require processing before it can be applied to a voice recognition engine 620 included in the server 614. Processing may include filtering to reduce or eliminate background noises present in the audio file 604. Such background noises may have been present during dictation. Processing may also include, but is not limited to, the reduction or elimination of reverb or vibration noises present in the audio file 604. Processing as just described may take place in an audio file filter 622, which may be implemented in software. Processing may also include converting the sampling rate of the audio file 604 from one rate to another. For example, in the embodiment described in FIG. 6, the audio file 604 was recorded using a sampling rate of 11 kHz, however the voice recognition engine 620 requires an audio input having a sampling rate of 22 kHz. Therefore, in the embodiment of FIG. 6, a conversion of sampling rate from 11 kHz to 22 kHz is required. Of course, conversions from one sampling rate to another may not be necessary and conversions from any given sampling rate to sampling rates other than those disclosed are also acceptable without departing from the scope of the invention. In the embodiment of FIG. 6, sampling rate conversion may occur in an audio file interpreter 623, and may be handled in software.

In an embodiment, the audio file is processed as described above, and then input to a voice recognition engine 620 (similar to 334 FIG. 3) for generation of an editable text file 624, an audio file 626, and synchronization file 630 (similar to 352 FIG. 3). As previously described, processing results in the generation of a read-only text file 632 and the deletion of the audio file 626, editable text file 624, and synchronization file 630. User voice model 634 and specialty specific vocabulary 636 may be used by the voice recognition engine 630 during the process of transcribing the audio file 604 into the editable text file 624.

Figure 7:
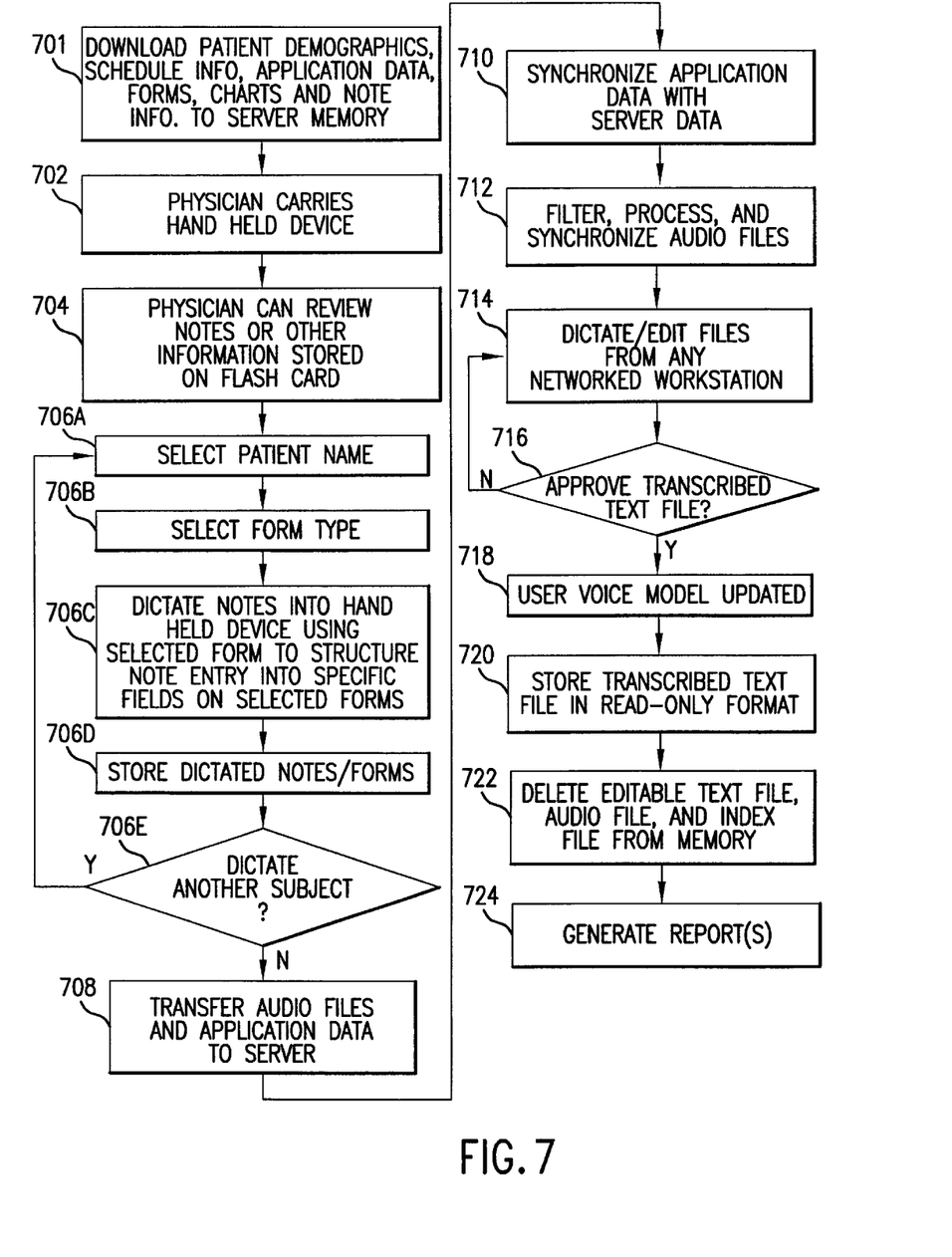
FIG. 7 is a flow diagram illustrating yet another method of operation in accordance with an embodiment of the invention.

FIG. 7 is a flow diagram illustrating yet another method of operation in accordance with an embodiment of the invention. At step 701, patient demographics, schedule information, application data, forms, charts and note information may be downloaded to the handheld device from a server via a data transfer mechanism. At step 702, the physician may carry the handheld device as he performs his duties. At step 704, the physician has the ability to review previous notes related to any data stored on the handheld device.

The physician may wish to dictate a new note. At step 706A, a patient's name may be selected by tapping on the displayed name in a list of names with a stylus on the handheld computing device screen, or by navigating the list by rotating a wheel on the side of the unit, or by other suitable means of selection. At step 706B, a form type to be dictated is selected. At step 706C, the physician may dictate notes into the handheld device using the selected form to structure note entry into specific fields on selected forms. Dictation may begin by depressing and releasing, or depressing and holding, the record button on the handheld computing device and thereafter beginning dictation. Macros and other voice commands can be used during dictation. Also, the user can navigate through sections, or fields, of a form by tapping on a desired section with the stylus on the handheld computing device screen, or navigate through the sections by rotating a wheel on the side of the unit, or other suitable means of selection. At step 706D, the dictated notes or forms (for example, in the form of application data and audio files) may be stored in a memory of the handheld device. At step 706E, the physician may repeat steps 706A through 706D for the same or other patients (i.e., dictation subjects).

At step 708, which may be at the day's conclusion or at any point during the day, the physician may transfer audio files and application data to a server via a data transfer mechanism. At step 710, the transferred application data is synchronized with the server's application data. At step 712, audio files are filtered, processed, and synchronized for storage and further processing or editing on the server. Further processing includes processing of the audio file in a voice recognition engine to generate transcribed text that is stored in an editable transcribed text file. An index file is also generated. The index file associates each word of text in the editable transcribed text file with the location of a sound in the audio file.

At step 714, a first user (e.g., any network user) from any networked workstation in communication with the server can add dictation to any given field in any given note or form. In an embodiment, free-form dictation for the given field may be limited to the first user, while any other authorized user (i.e., a second user) may be limited to dictating corrections to the text for that given field. The second user may, of course, enter free-form dictation into any other empty field. In addition, at step 714, any user from any networked workstation in communication with the server can edit any given field in any given note or form. Editing may involve the use of the synchronized audio file, which, as described in other embodiments herein, can be used to allow the editor to hear the recorded voice of the person that dictated the text in question. An editor may select a word or group of words for recorded audio playback. The editor may make corrections and/or alterations to the editable transcribed text file. At step 716, the transcribed text in the editable transcribed text file may be approved. If the transcribed text is not approved, then the user may return to step 714 for further dictation and/or editing of the transcribed text. If the transcribed text is approved, then at step 718 the voice models of the users that provided dictation to create the note or form are updated. At step 720, the approved transcribed text is stored in file in a read-only format. The read-only file may be signed and stored as an electronic signature. At step 722 the editable transcribed text file, audio file, and index file are deleted from the memory of the server. At step 724, reports may be generated.

The disclosed embodiments are illustrative of the various ways in which the present invention may be practiced. Other embodiments can be implemented by those skilled in the art without departing from the spirit and scope of the present invention.

What is claimed is:

1. A method of generating text including variable data in an electronic spoken dictation-to-text system, comprising:
    converting spoken dictation to a first string of text in a voice recognition engine;
    decoding a macro name in the first string of text, the macro name having associated therewith a second string of text and a variable value;
    prompting a user for the variable value;
    converting additional spoken dictation to a third string of text in the voice recognition engine, the third string of text comprising a representation of the variable value; and
    combining the second string of text with the third string of text.

2. The method of claim 1, wherein the voice recognition engine generates strings of text such that each transcribed letter of spoken dictation in a string of text is referenced to a location, and thus a sound, in an associated audio file.

3. The method of claim 1, wherein the prompting comprises one of an audible cue, a visual cue, and a combined audible and visual cue.

4. The method of claim 1, wherein combining comprises one of insertion of the third string of text within the second string of text, appending the third string of text to the second string of text, and appending the second string of text to the third string of text.

5. A method of generating a document from spoken dictation of a user, comprising:
    acquiring data related to a plurality of dictation subjects;
    populating a database with the acquired data related to the plurality of dictation subjects;
    receiving identification of a first document from a plurality of documents, the first document having a plurality of fields for data entry;
    receiving identification of a first field in the plurality of fields for data entry;
    receiving dictated voice into an audio input device;
    generating, by a voice recognition engine operatively coupled to the audio input device, a first audio portion and a first text portion from the dictated voice, wherein the first audio portion and the first text portion are associated with the first field for data, and wherein the first audio portion is stored in an audio file and the first text portion is stored in an editable text file;
    storing the audio file and editable text file in a first logical memory location;
    receiving edits to the first text portion; and
    storing the edited first text portion as a second document in a second logical memory location.

6. The method of claim 5, wherein the second document is a read-only document.

7. The method of claim 5, wherein acquiring data related to a plurality of dictation subjects includes a real-time download of the data related to the plurality of dictation subjects.

8. The method of claim 5, wherein acquiring data related to a plurality of dictation subjects includes a pull of data on demand of data related to one of the plurality of dictation subjects.

9. The method of claim 7, wherein the real time download comprises use of a communication interface, wherein the communication interface is one of a modem, a LAN (local area network) an Internet connection, a wireless connection, a removable data storage device, and a hard wired link.

10. The method of claim 9, wherein the wireless connection is one of a radio wave connection, a light wave connection, and an infrared connection.

11. The method of claim 8, wherein the real time download comprises use of a communication interface, wherein the communication interface is one of a modem, a LAN (local area network) interface, an Internet connection, a wireless connection, a removable data storage device, and a hard wired link.

12. The method of claim 11, wherein the wireless connection is one of a radio wave connection, a light wave connection, and an infrared connection.

13. The method of claim 5, wherein the voice recognition engine generates the first text portion such that each transcribed letter of dictated voice stored in the editable text file is referenced to a location, and thus a sound, in the audio file.

14. The method of claim 5, further comprising deletion of the audio file and the editable text file after the step of storing the edited first text portion as a read-only document.

15. The method of claim 5, wherein receiving edits to the first text portion include newly spoken voice dictation from another user, different from the user.

16. A machine readable medium having stored thereon a plurality of executable instructions, the plurality of instructions comprising instructions to:

acquire data related to a plurality of dictation subjects;

populate a database with the acquired data related to the plurality of dictation subjects;

receive identification of a first document from a plurality of documents, the first document having a plurality of fields for data entry;

receive identification of a first field in the plurality of fields for data entry;

receive dictated voice into an audio input device;

generate, by a voice recognition engine operatively coupled to the audio input device, a first audio portion and a first text portion from the dictated voice, wherein the first audio portion and the first text portion are associated with the first field for data, and wherein the first audio portion is stored in an audio file and the first text portion is stored in an editable text file;

store the audio file and editable text file in a first logical memory location;

receive edits to the first text portion; and store the edited first text portion as a second document in a second logical memory location.

17. The machine readable medium of claim 16, wherein the second document is a read-only document.

18. The machine readable medium of claim 16, wherein the instruction to acquire data related to a plurality of dictation subjects includes a real-time download of the data related to the plurality of dictation subjects.

19. The machine readable medium of claim 16, wherein the instruction to acquire data related to a plurality of dictation subjects includes a pull of data on demand of data related to one of the plurality of dictation subjects.

20. The machine readable medium of claim 18, wherein the real time download comprises use of a communication interface, wherein the communication interface is one of a modem, a LAN (local area network) an Internet connection, a wireless connection, a removable data storage device, and a hard wired link.

21. The machine readable medium of claim 20, wherein the wireless connection is one of a radio wave connection, a light wave connection, and an infrared connection.

22. The machine readable medium of claim 19, wherein the real time download comprises use of a communication interface, wherein the communication interface is one of a modem, a LAN (local area network) interface, an Internet connection, a wireless connection, a removable data storage device, and a hard wired link.

23. The machine readable medium of claim 22, wherein the wireless connection is one of a radio wave connection, a light wave connection, and an infrared connection.

24. The machine readable medium of claim 16, wherein the voice recognition engine generates the first text portion such that each transcribed letter of dictated voice stored in the editable text file is referenced to a location, and thus a sound, in the audio file.

25. The machine readable medium of claim 16, further comprising instructions to delete the audio file and the editable text file after the instructions to store the edited first text portion as a read-only document.

26. The machine readable medium of claim 16, wherein edits to the first text portion include newly spoken voice dictation from another user, different from the user.

27. A method of generating a document by dictation to a handheld computing device, comprising:

selecting, by a first user at the handheld computing device:
a first dictation subject from a set of dictation subjects,
application data having a plurality of fields for data entry, and
a first field from the plurality of fields;

dictating, by the first user, speech into the handheld computing device, wherein the dictated speech is associated by an index with the first field;

repeating the dictating and associating for other fields in the plurality of fields;

storing the dictated speech as an audio file, the index, and the application data in a memory of the handheld computing device;

transferring the audio file, index, and application data to a memory of a server via a data transfer mechanism;

processing, at the server, the audio file content in a voice recognition engine to generate transcribed text associated with the plurality of fields of the application data in accordance with the index;

storing the processed audio file content as an editable transcribed text file;

editing, by a second user having access to the server, the editable transcribed text file;

updating a voice model of the first user based on editing by the second user;

storing the editable transcribed text file as a read-only transcribed text file in a read-only format;

deleting the editable transcribed text file, index, and audio file from the memory of the server; and generating a report from the read-only transcribed text file.

* * * * *